(12) United States Patent
Razavi et al.

(10) Patent No.: US 9,302,099 B2
(45) Date of Patent: Apr. 5, 2016

(54) SYSTEM AND METHOD FOR EVALUATING LEAD STABILITY OF AN IMPLANTABLE MEDICAL DEVICE

(71) Applicant: Pacesetter, Inc., Sunnyvale, CA (US)

(72) Inventors: Hoda Razavi, San Jose, CA (US); Yelena Nabutovsky, Mountain View, CA (US); Rohan A. More, Los Angeles, CA (US); Kyungmoo Ryu, Palmdale, CA (US); Luke C. McSpadden, Los Angeles, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/703,760

(22) Filed: May 4, 2015

(65) Prior Publication Data

US 2015/0314121 A1 Nov. 5, 2015

Related U.S. Application Data

(60) Provisional application No. 61/988,774, filed on May 5, 2014.

(51) Int. Cl.
*A61N 1/00* (2006.01)
*A61N 1/05* (2006.01)

(52) U.S. Cl.
CPC ......... *A61N 1/057* (2013.01); *A61N 2001/0578* (2013.01)

(58) Field of Classification Search
CPC .................. A61N 1/057; A61N 2001/0578
See application file for complete search history.

(56) References Cited

U.S. PATENT DOCUMENTS

| | | |
|---|---|---|
| 5,391,199 A | 2/1995 | Ben-Haim |
| 6,233,476 B1 | 5/2001 | Strommer et al. |
| 6,301,496 B1 | 10/2001 | Reisfeld |
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,397 B2 | 8/2007 | Hauck et al. |
| 7,276,064 B2 | 10/2007 | Paul et al. |
| 7,338,486 B2 | 3/2008 | Sliwa et al. |

(Continued)

FOREIGN PATENT DOCUMENTS

| | | |
|---|---|---|
| EP | 1 070 480 A2 | 1/2001 |
| EP | 1 508 300 A1 | 2/2005 |

(Continued)

OTHER PUBLICATIONS

Notice of Allowance mailed Oct. 27, 2015; Related U.S. Appl. No. 14/328,523.

(Continued)

*Primary Examiner* — George Manuel
(74) *Attorney, Agent, or Firm* — Theresa A. Raymer

(57) ABSTRACT

A method and system are provided that provide feedback regarding lead stability for a candidate target vessel, and provide guidance on a type of lead to be used. The method and system utilize a surgical navigation system and information regarding patient anatomy to predict lead stability within the patient anatomy. The method and system provide patient-specific force measurements for one or more vessels of a patient.

20 Claims, 3 Drawing Sheets

(56) References Cited

U.S. PATENT DOCUMENTS

| | | | |
|---|---|---|---|
| 7,386,339 B2 | 6/2008 | Strommer et al. | |
| 7,505,809 B2 | 3/2009 | Strommer et al. | |
| 7,697,973 B2 | 4/2010 | Strommer et al. | |
| 7,881,769 B2 | 2/2011 | Sobe | |
| 8,016,764 B1 | 9/2011 | Shelchuk | |
| 2003/0093067 A1 | 5/2003 | Panescu | |
| 2003/0233039 A1 | 12/2003 | Shao et al. | |
| 2005/0154282 A1 | 7/2005 | Li et al. | |
| 2006/0245536 A1 | 11/2006 | Boing | |
| 2007/0073179 A1 | 3/2007 | Afonso et al. | |
| 2007/0100332 A1 | 5/2007 | Paul et al. | |
| 2007/0106146 A1 | 5/2007 | Altmann et al. | |
| 2007/0181139 A1 | 8/2007 | Hauck | |
| 2007/0244479 A1 | 10/2007 | Beatty et al. | |
| 2007/0270705 A1 | 11/2007 | Starks | |
| 2008/0009758 A1 | 1/2008 | Voth | |
| 2008/0091193 A1 | 4/2008 | Kauphusman et al. | |
| 2009/0163904 A1 | 6/2009 | Miller et al. | |
| 2009/0171345 A1 | 7/2009 | Miller et al. | |
| 2010/0168550 A1 | 7/2010 | Byrd et al. | |
| 2010/0268059 A1 | 10/2010 | Ryu | |
| 2011/0243401 A1 | 10/2011 | Zabair et al. | |
| 2012/0184863 A1 | 7/2012 | Harlev et al. | |
| 2013/0222415 A1 | 8/2013 | Vilsmeier | |
| 2013/0272592 A1 | 10/2013 | Eichler et al. | |
| 2015/0045867 A1* | 2/2015 | Krishnan et al. | 607/119 |
| 2015/0133802 A1 | 5/2015 | Nabutovsky et al. | |
| 2015/0141765 A1 | 5/2015 | Razavi et al. | |
| 2015/0141858 A1 | 5/2015 | Razavi et al. | |

FOREIGN PATENT DOCUMENTS

| | | |
|---|---|---|
| EP | 2 757 528 A1 | 7/2014 |
| WO | 97/24981 A2 | 7/1997 |
| WO | 2012/090148 A1 | 7/2012 |

OTHER PUBLICATIONS

Notice of Allowance mailed Jun. 22, 2015; Related U.S. Appl. No. 14/328,523.

Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.

International Search Report and Written Opinion in PCT Application No. PCT/US2015/028206 (Jul. 22, 2015).

Quatember, Bernhard et al., "Geometric Modeling and Motion Analysis of the Epicardial Surface of the Heart", Mathematics and Computers in Simulation, vol. 81, No. 3, pp. 608-622, Nov. 2010.

Segars, W. Paul et al., "A Realistic Spline-Based Dynamic Heart Phantom", IEEE Transactions on Nuclear Science vol. 46, No. 3, pp. 503-506, Jun. 1999.

U.S. Appl. No. 09/107,731, filed Jun. 30, 1998 for "Chamber Mapping System".

Advisory Action mailed Aug. 10, 2015; Related U.S. Appl. No. 12/347,216.

Amendment filed Jun. 25, 2015; Related U.S. Appl. No. 12/347,216.

Final Office Action mailed May 4, 2015; Related U.S. Appl. No. 12/347,216.

Amendment filed Dec. 18, 2014; Related U.S. Appl. No. 12/347,216.

Non-Final Office Action mailed Oct. 2, 2014; Related U.S. Appl. No. 12/347,216.

Advisory Action mailed May 1, 2014; Related U.S. Appl. No. 12/347,216.

Amendment filed Apr. 24, 2014; Related U.S. Appl. No. 12/347,216.

Applicant Interview Summary, Apr. 21, 2014; Related U.S. Appl. No. 12/347,216.

Final Office Action mailed Feb. 25, 2014; Related U.S. Appl. No. 12/347,216.

Amendment filed Feb. 4, 2014; Related U.S. Appl. No. 12/347,216.

Non-Final Office Action mailed Nov. 21, 2013; Related U.S. Appl. No. 12/347,216.

Amendment filed Oct. 29, 2012; Related U.S. Appl. No. 12/347,216.

Advisory Action mailed Oct. 11, 2012; Related U.S. Appl. No. 12/347,216.

Amendment filed Oct. 1, 2012; Related U.S. Appl. No. 12/347,216.

Advisory Action mailed Sep. 12, 2012; Related U.S. Appl. No. 12/347,216.

Amendment filed Aug. 28, 2012; Related U.S. Appl. No. 12/347,216.

Final Office Action mailed Jun. 29, 2012; Related U.S. Appl. No. 12/347,216.

Amendment filed May 14, 2012; Related U.S. Appl. No. 12/347,216.

Interview Summary, Feb. 28, 2012; Related U.S. Appl. No. 12/347,216.

Non-Final Office Action mailed Feb. 13, 2012; Related U.S. Appl. No. 12/347,216.

Non-Final Office Action mailed Sep. 30, 2015; Related U.S. Appl. No. 14/270,181.

Notice of Allowance mailed Dec. 8, 2015; Related U.S. Appl. No. 12/347,216.

Final Office Action mailed Jan. 22, 2016; Related U.S. Appl. No. 14/270,176.

Non-Final Office Action mailed Feb. 8, 2016; Related U.S. Appl. No. 14/270,181.

* cited by examiner

SYSTEM AND METHOD FOR EVALUATING LEAD STABILITY OF AN IMPLANTABLE MEDICAL DEVICE

RELATED APPLICATION DATA

The present application relates to and claims priority from U.S. provisional application Ser. No. 61/988,774, filed May 5, 2014, entitled "SYSTEM AND METHOD FOR EVALUATING LEAD STABILITY OF AN IMPLANTABLE DEVICE," which is hereby expressly incorporated by reference in its entirety.

BACKGROUND OF THE DISCLOSURE

Embodiments of the present disclosure generally relate to systems and methods for evaluating lead stability of an implantable medical device.

Lead dislodgement is a common complication of cardiac resynchronization therapy (CRT) implants that may lead to increased capture thresholds, loss of capture, reduced biventricular pacing, and reduced response. Depending on the severity of the dislodgement, there is typically a need for re-intervention to re-stabilize the lead, which may lead to further complications. Possible causes of lead dislodgement include twiddler syndrome, device migration especially in obese patients, and excessive movement due to cardiac and/or respiratory motion, especially during hyperapnea.

The St. Jude Medical MediGuide™ (MDG) cardiovascular navigation system is a 3-D electromagnetic navigation system that provides real-time position and orientation of MDG sensors embedded in electrophysiological tools. The MDG system may be integrated with a fluoroscopic imaging system and tracks the sensors continuously within the imaging volume of the fluoroscopic system, on both live fluoroscopy and pre-recorded backgrounds.

SUMMARY

Embodiments of the present disclosure provide systems and methods for predicting lead stability in candidate vessels at the time of implant in order to guide a physician to an optimal implant site and to recommend which lead to use.

Certain embodiments of the present disclosure provide a method that may include providing feedback regarding lead stability for a candidate target vessel, and providing guidance on a type of lead to be used.

Certain embodiments of the present disclosure provide a method that may include utilizing a surgical navigation system and information regarding patient anatomy to predict lead stability within the patient anatomy.

Certain embodiments of the present disclosure provide a method that may include providing patient-specific force measurements for one or more vessels of a patient.

Certain embodiments of the present disclosure provide a system for determining a lead placement site within patient anatomy. The system may include at least one processor configured to calculate a lead stability index (LSI) relating to a lead placement site for one or more candidate vessels, and a display operatively coupled to the at least one processor. The display is configured to show data related to the lead placement site. The processor(s) may be configured to display the data related to the lead placement site on the display as color-coded data.

The processor(s) may be configured to calculate the LSI through the following equation:

$$LSI = \kappa \frac{T \cdot L}{a \cdot \alpha}$$

where T is a measure of vessel tortuosity, L is a vessel length, a is a largest second derivative of the three-dimensional (3-D) motion experienced by the vessel, $\alpha$ is an ostial take-off angle, and $\kappa$ is a constant.

In at least one embodiment, the processor(s) may be configured to calculate the LSI through the following equation:

$$LSI = \kappa \frac{T \cdot L}{a \cdot \alpha \cdot s \cdot \Delta P}$$

where T is a measure of vessel tortuosity, L is a vessel length, a is a largest second derivative of the three-dimensional (3-D) motion experienced by the vessel, $\alpha$ is an ostial take-off angle, $\kappa$ is a constant, s is a maximum lead body mechanical stress, and $\Delta P$ is a blood pressure differential from a tip to an ostium of the vessel.

The processor(s) may be configured to calculate the LSI of the one or more candidate vessels based on motion and anatomical measurements in each of the one more candidate vessels. The processor(s) may be configured to calculate the LSI, at least in part, by accounting for one or more of (a) acceleration experienced by the one or more candidate vessels, (b) vessel tortuosity, (c) vessel length, and/or (d) ostial angle.

Certain embodiments of the present disclosure provide a method for determining a lead placement site within patient anatomy. The method may include calculating a lead stability index (LSI) relating to lead placement site for one or more candidate vessels, and displaying data related to the lead placement site.

DETAILED DESCRIPTION

The foregoing summary, as well as the following detailed description of certain embodiments will be better understood when read in conjunction with the appended drawings. As used herein, an element or step recited in the singular and preceded by the word "a"or "an"should be understood as not necessarily excluding the plural of the elements or steps. Further, references to "one embodiment"are not intended to be interpreted as excluding the existence of additional embodiments that also incorporate the recited features. Moreover, unless explicitly stated to the contrary, embodiments "comprising" or "having"an element or a plurality of elements having a particular property may include additional elements not having that property.

Embodiments herein may be implemented with, and/or utilize aspects of, the methods and system described in the following applications:

- U.S. patent application Ser. No. 14/328,523, filed Jul. 10, 2014, titled "METHOD AND SYSTEM TO ASSESS MECHANICAL DYSSYNCHRONY BASED ON MOTION DATA COLLECTED BY A NAVIGATION SYSTEM"now U.S. Patent Pub. No. 2015/0133802,
- U.S. patent application Ser. No. 14/328,513, filed Jul. 10, 2014, titled "METHOD AND SYSTEM TO MEASURE CARDIAC MOTION USING A CARDIOVASCULAR NAVIGATION SYSTEM"now U.S. Patent Pub. No. 2015/0141858,
- U.S. patent application Ser. No. 14/478,707, filed Sept. 5, 2014, titled "METHOD AND SYSTEM TO IDENTIFY MOTION DATA ASSOCIATED WITH CONSISTENT ELECTRICAL AND MECHANICAL BEHAVIOR FOR A REGION OF INTEREST"now U.S. Patent Pub. No. 2015/0141765,
- U.S patent application 61/988,779, filed May 5, 2014, titled "METHODS AND SYSTEMS TO CALCULATE TIME OF MECHANICAL ACTIVATION USING CHARACTERICATION MOTION DATA AREA STRAINS",
- U.S. patent application Ser. No. 14/270,181, filed May 5, 2014, titled "METHOD AND SYSTEM TO CHARACTERIZE MOTION DATA BASED ON NEIGHBORING MAP POINTS"now U.S. Patent Pub. No. 2015/0313511,
- U.S. patent application Ser. No. 14/270,186, filed May 5, 2014titled "METHOD AND SYSYTEM FOR CACLULATING STRAIN FROM CHARACTERIZATION DATA OF A CARDIAC CHAMBER", now U.S. Patent Pub. No. 2015/0313480,
- U.S. patent application Ser. No. 14/270,176, filed May 5, 2014, titled "METHOD AND SYSTEM FOR DISPLAYING A THREE DIMENSIONAL VISUALIZATION OF CARDIAC MOTION", now U.S. Patent Pub. No. 2015/0313510,
- U.S. patent application 61/988,735, filed May 5, 2014, titled "METHOD AND SYSTEM TO DETERMINE CARDIAC CYCLE LENGTH IN CONNECTION WITH CARDIAC MAPPING",
- U.S. pat application 61/988,763, filed May 5, 2014, titled "METHOD AND SYSTEM TO EQUALIZING CARDIAC CYCLE LENGTH BETWEEN MAP POINTS",
- U.S. pat application 61/988,767, filed May 5, 2014, titled "METHOD AND SYSTEM TO SUBDIVIDE A MAPPING AREA FOR MECHANICAL ACTIVATION ANALYSIS", and
- U.S. pat application 61/988,771, filed May 5, 2014, titled "CARDIAC RESYNCHRONIZATION SYSTEM AND METHOD".

All of the above cited applications are expressly incorporated herein by reference in their entireties.

Figure 1:
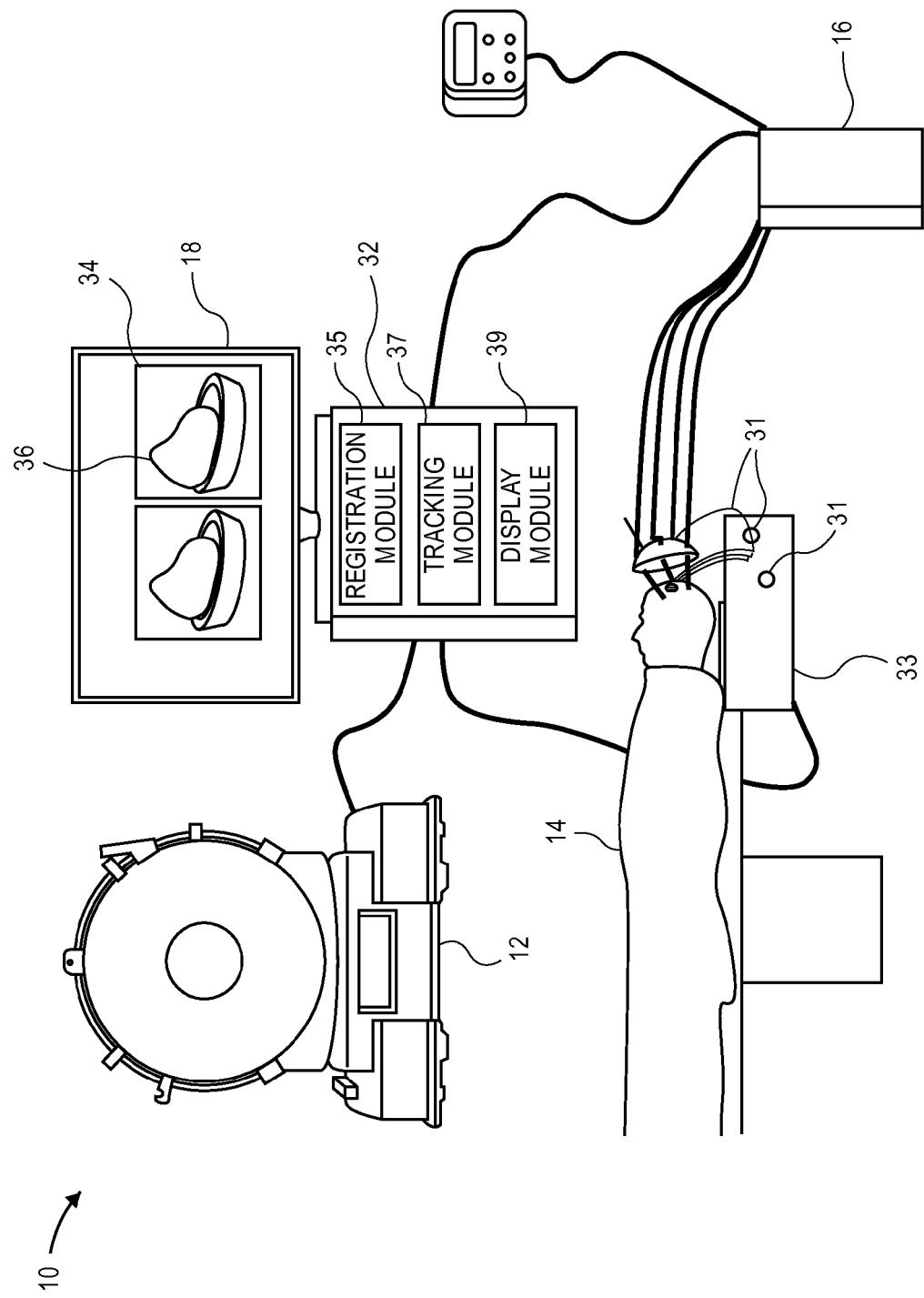
FIG. 1 illustrates a schematic diagram of a system 10, according to an embodiment of the present disclosure.

FIG. 1 illustrates a schematic diagram of a system 10, according to an embodiment of the present disclosure. The system 10 may include an imaging sub-system 12 configured to acquire images of a patient 14, a positioning sub-system 16, and a surgical navigation sub-system 18. The imaging sub-system 12 is used to acquire one or more images of the patient 14. For example, the imaging sub-system 12 is configured to acquire one or more images of a heart of a patient. The positioning sub-system 16 may be used to position probes, sensors, leads, and the like into the patient 14. The surgical navigation sub-system 18 may be used in conjunction with the acquired images to allow a surgeon to visualize placement of the probes of the positioning sub-system 16 into the patient 14. Alternatively, the system 10 may not include the positioning sub-system 16. Further, the system may be used with respect to imaging and navigation with respect to other anatomical structure of the patient other than the heart.

The imaging sub-system 12 may include one or more of an X-ray, fluoroscope, CT, MRI, Positron Emission Tomography (PET), ultrasound, or other such imaging systems. For example, the imaging sub-system 12 may include MRI and CT imaging systems. In general, the imaging sub-system 12 may include a radiation source or generator and a radiation sensor or detector.

The surgical navigation sub-system 18 may include a main housing 32, such as a computer workstation, operatively connected to a display 34 that is configured to display images 36 thereon. The display 34 may be or include a monitor, screen, television, or the like, for example. The surgical navigation sub-system 18 may be used to electromagnetically track movement of probes of the positioning sub-system 16 before and during a procedure. The surgical navigation sub-system 18 may be used to automate surgical planning and lead or probe placement, while displaying a current position of the lead or probe within the patient anatomy.

The main housing 32 may contain a registration module 35, a tracking module 37, and a display module 39. The registration module 35 may be configured to register reference members, such as fiducials, coils, and/or the like, of a frame, probe, or the like, with one or more reference markers, points, or the like of images of patient anatomy. The tracking module 37 is configured to track movement of a probe, for example, with respect to an area or volume, such as within the heart. The display module 39 is configured to display a representation of the probe, for example, on one or more acquired images on the display, based on the movement of the probe as determined by the tracking module 37.

Each of the modules 35, 37, and 39 may include any processor-based or microprocessor-based system including systems using microcontrollers, reduced instruction set computers (RISC), application specific integrated circuits (ASICs), logic circuits, and any other circuit or processor capable of executing the functions described herein. For example, each of the modules 35, 37, and 39 may be or include at least one processor and at least one memory. The above are exemplary only, and are thus not intended to limit in any way the definition and/or meaning of the term "computer" or "module."

The surgical navigation sub-system 18 may also include a tracking assembly 33 in the vicinity of the patient 14. For example, the tracking assembly 33 may include a housing situated on or underneath a platform on which the patient 14 rests. The tracking assembly 33 may include one or more transmitters 31 configured to radiate a field, such as an electromagnetic field, within the vicinity of the patient 14. The field radiated by the transmitters 31 may be detected by a position detector of a probe, for example, as described below.

The surgical navigation sub-system 18 may be used with various anatomical structures. For example, the surgical navigation sub-system 18 may be used to track movement of devices, instruments, probes, and the like within the heart of the patient.

The surgical navigation sub-system may be further described with respect to U.S. Pat. No. 7,811,294, entitled "Automatic Guidewire Maneuvering System and Method," which is hereby incorporated by reference in its entirety. The surgical navigation sub-system may be used to visualize movement of the probe with respect to one or more images of the heart. The surgical navigation sub-system may be used to automatically move a probe according to a surgical plan.

Optionally, the surgical navigation sub-system may be used to simply superimpose an image of the probe with respect to the image(s) of the heart, brain, or the like in order to track movement of the surgical probe with respect thereto.

Figure 2:
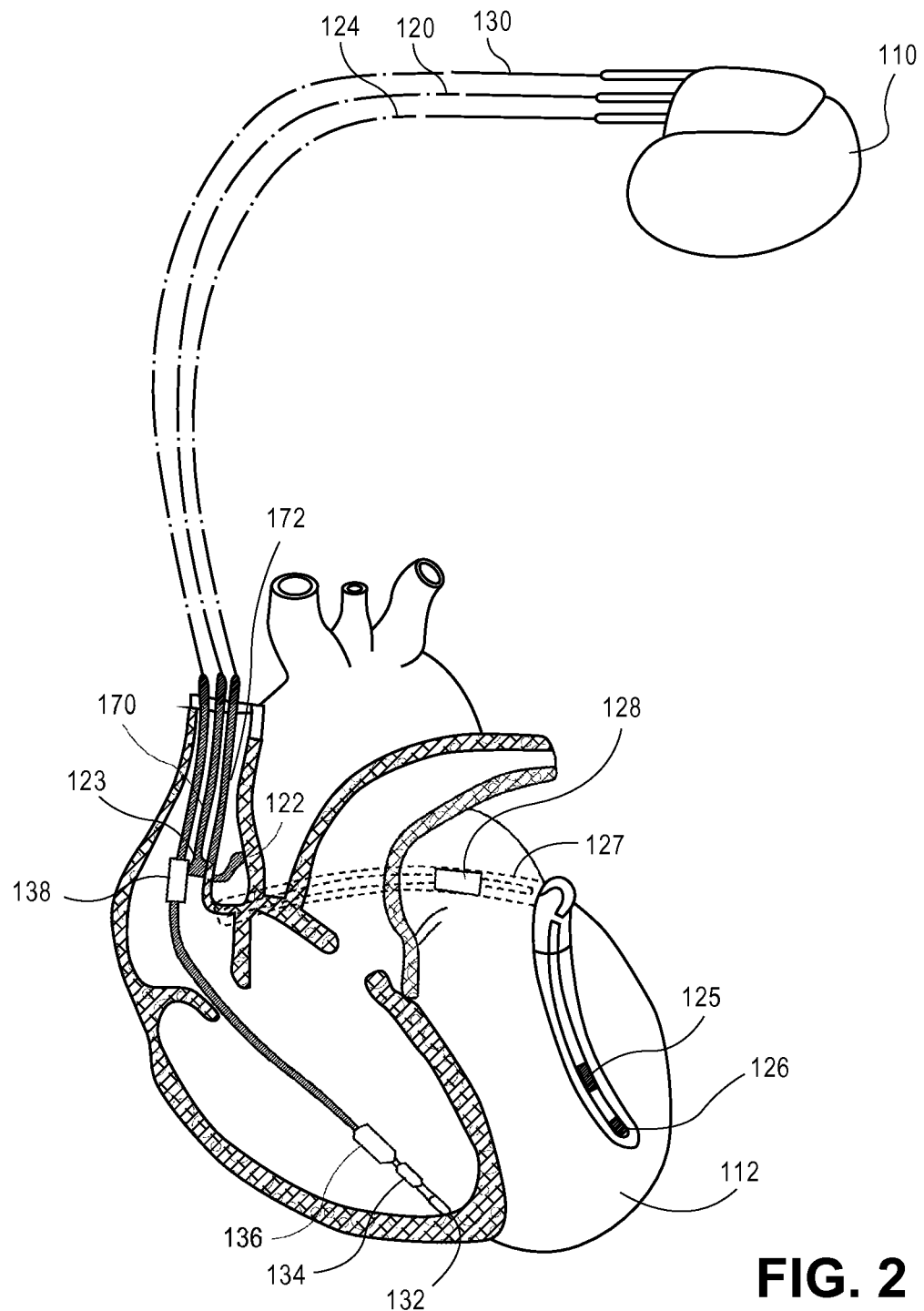
FIG. 2 illustrates a simplified view of an exemplary implantable medical device (IMD) in electrical communication with at least three leads implanted into a patient's heart, according to an embodiment of the present disclosure.

FIG. 2 illustrates an IMD 110 in electrical communication with a patient's heart 112 by way of three leads 120, 124 and 130 suitable for delivering multi-chamber stimulation and/or shock therapy. To sense atrial cardiac signals and to provide right atrial chamber stimulation therapy, the IMD 110 is coupled to an implantable right atrial (RA) lead 120 including at least one atrial tip electrode 122 that typically is implanted in the patient's right atrial appendage. The right atrial lead 120 may also include an atrial ring electrode 123 to allow bipolar stimulation or sensing in combination with the atrial tip electrode 122.

To sense the left atrial and left ventricular cardiac signals and to provide left-chamber stimulation therapy, the IMD 110 is coupled to a lead 124 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the lead 124 is designed to: receive atrial and/or ventricular cardiac signals; deliver left ventricular pacing therapy using at least one left ventricular tip electrode 126 for unipolar configurations or in combination with left ventricular ring electrode 125 for bipolar configurations; and/or deliver left atrial pacing therapy using at least one left atrial ring electrode 127 as well as shocking therapy using at least one left atrial coil electrode 128.

The IMD 110 is also shown in electrical communication with the patient's heart 112 by way of an implantable right ventricular (RV) lead 130 including, in the embodiment, a right ventricular (RV) tip electrode 132, a right ventricular ring electrode 134, a right ventricular coil electrode 136, a superior vena cava (SVC) coil electrode 138, and so on. Typically, the right ventricular lead 130 is inserted transvenously into the heart 112 so as to place the right ventricular tip electrode 132 in the right ventricular apex such that the RV coil electrode 136 is positioned in the right ventricle and the SVC coil electrode 138 will be positioned in the right atrium and/or superior vena cava. Accordingly, the right ventricular lead 130 is capable of receiving cardiac signals, and delivering stimulation in the form of pacing and shock therapy to the right ventricle.

The IMD may be one of various types of implantable devices, such as, for example, an implantable pacemaker, implantable cardioverter-defibrillator ("ICD"), neurostimulator, electrophysiology ("EP") mapping and radio frequency ("RF") ablation system, or the like. Optionally, the IMD may be configured to provide leadless therapy.

Referring to FIGS. 1 and 2, the surgical navigation sub-system and/or at least one processor (which may be contained within the surgical navigation sub-system or another sub-system) may be used to guide a lead to an implant site, such as within a heart of a patient. Before placement of the LV lead, a lead stability index (LSI) may be calculated for each candidate vessel that may guide the physician to the site of LV lead placement, as well as provide guidance on the type of lead to be implanted. The information may be conveyed to the physician in a visual manner, such as through color-coding of the geometry, and in a quantitative manner by providing the LSI score. LSI parameters may be measured by placing an MDG-enabled tool along the length of the candidate target branches. LSI may be calculated as $$LSI = \kappa \frac{T \cdot L}{a \cdot \alpha}$$

Where T is a measure of vessel tortuosity, L is the vessel length, a is the largest second derivative of the three-dimensional (3-D) motion experienced by the vessel, α is the ostial take-off angle, and κ is a constant.

The LSI measurements may be refined through processes that include the addition of maximum lead body mechanical stress (s) and the blood pressure differential from the tip to the ostium of the vessel (ΔP). If these measurements are used, then LSI may be calculated as follows:

$$LSI = \kappa \frac{T \cdot L}{a \cdot \alpha \cdot s \cdot \Delta P}$$

In the case of patient-specific computational modeling of lead stress measurements, different lead types may be evaluated and the lead type with the highest LSI score may be recommended.

Figure 3:
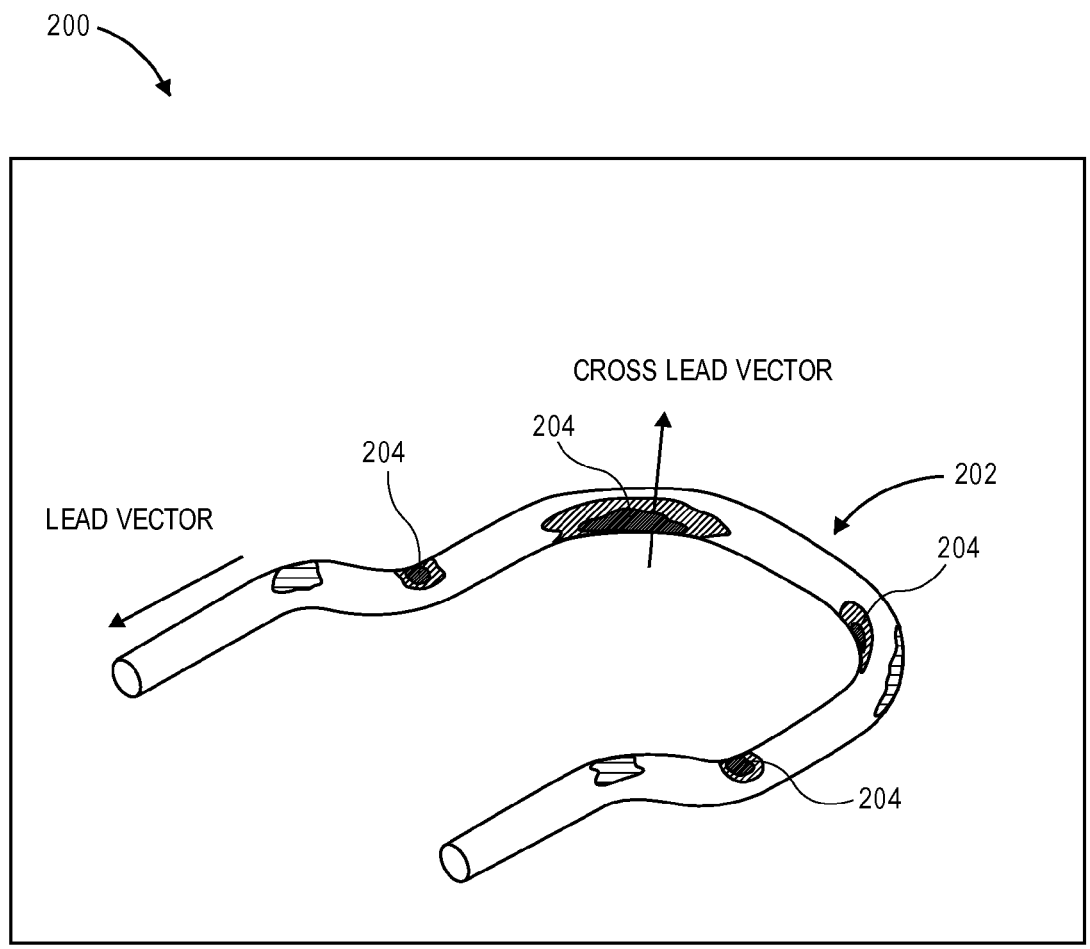
FIG. 3 illustrates a display showing a vessel, according to an embodiment of the present disclosure.

FIG. 3 illustrates a display 200 showing a vessel 202, according to an embodiment of the present disclosure. The display 200 may be display 34, or a portion thereof. As shown, embodiments of the present disclosure may show the vessel 202 having areas identified with different indicia. For example, various areas of the vessel 202 may be color-coded to indicate desirability (or lack thereof) of lead placement. For example, the areas 204 may include specific indicia, such as different colors, that may indicate that they are less than desirable for lead placement. For example, the areas 204 may be areas of higher stress, strain, or the like.

Referring to FIGS. 1-3, before placement of the LV lead, the surgical navigation system, such as an MDG system, calculates a lead stability index (LSI) of candidate vessels based on motion and anatomical measurements in each vessel. The lower the LSI index, the higher the likelihood of lead dislodgement. Based on these measurements, as well as motion measurements, an optimal site of LV lead placement may be recommended to the physician. In order to calculate the LSI, the following parameters may be measured or taken into account:

Acceleration (a): using an MDG-enabled tool such as a MDG-enabled guidewire, the motion of the vessel and therefore the lead may be measured during different phases of the cardiac and respiratory cycles. The second derivative of the 3D motion signals (x,y,z) may then be calculated to obtain 3 acceleration signals. The parameter a may be the maximum acceleration among the three signals experienced by the vessel in any dimension at any point in the recording.

Vessel tortuosity (T): the trajectory of the MDG-enabled tool within the vessel may be evaluated to determine the degree of tortuosity. The more tortuous a vessel is with additional curves and bends, the more contact between the lead body and the vessel wall, the higher the frictional forces between their interfaces, and the more stable the lead. For a given bend below a certain pre-defined angle threshold (such as 60 degrees), a value of 1 may be added to the tortuosity value T.

Vessel length (L): the trajectory of the tool may be analyzed to determine the length of the vessel. The longer the vessel, the further the lead may be wedged into the vessel, and the higher the stability index.

Ostial angle ($\alpha$): a more acute take-off angle (in radians) at the target branch ostium increases lead stability.

With the above measurements, the LSI may be defined as (K is a scaling factor to be determined empirically)

$$LSI = \kappa \frac{T \cdot L}{a \cdot \alpha}$$

LSI may be further refined through lead body mechanical stress (s): if a point-by-point measurement of motion along the length of the vessel is possible, the internal strain of the lead may be calculated. With known lead geometry, mass, and material properties, the measured strains may be translated into mechanical stress using techniques such as assumed normalized values for all patients, or patient-specific computational modeling that takes all applied forces into account. If there are areas of high stress larger than a pre-defined threshold within the calculated stress profile of the lead, the LSI may be reduced as the lead body would move in response to the exerted stress. The parameter s is defined as the maximum stress experienced in any dimension. With this measurement, different lead geometries/designs may be considered and an optimal lead type may be recommended to the physician.

LSI may also be refined through blood pressure differential (AP): two blood pressure measurements may be taken, one at the distal end of the vessel and one at the proximal end of the vessel close to the target vein ostium. The higher the blood pressure differential within the vessel, the more blood flow, and therefore more forces are applied to the lead body. Higher AP may correspond to lower LSI.

Accordingly, LSI may be calculated as follows:

$$LSI = \kappa \frac{T \cdot L}{a \cdot \alpha \cdot s \cdot \Delta P}$$

In order to provide feedback on the stability likelihood of the lead in a particular vessel, a color-based visualization of the venogram or of a 3-D reconstruction of the vessel tree may be used. In this case, the LSI may be converted to a color that is projected onto the anatomy.

The computations and analyses described in the present application may be performed by one or more processors, which may include or be communicatively coupled to one or more memories.

Various embodiments described herein provide a tangible and non-transitory (for example, not an electric signal) machine-readable medium or media having instructions recorded thereon for one or more processors or computers to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the sub-systems, systems, control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description.

The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means –plus-function format and are not intended to be interpreted based on 35 U.S.C. §112(f), unless and until such claim limitations expressly use the phrase "means for" followed by a statement of function void of further structure.

What is claimed is:

1. A system for determining a lead placement site within patient anatomy, the system comprising:
at least one processor configured to calculate a lead stability index (LSI) relating to a lead placement site for one or more candidate vessels; and
a display operatively coupled to the at least one processor, wherein the display is configured to show data related to the lead placement site, and wherein the at least one processor is configured to display the data related to the lead placement site on the display as color-coded data.

2. The system of claim 1, wherein the at least one processor is configured to calculate the LSI through the following equation:

$$LSI = \kappa \frac{T \cdot L}{a \cdot \alpha}$$

where T is a measure of vessel tortuosity, L is a vessel length, a is a largest second derivative of the three-dimensional (3-D) motion experienced by the vessel, α is an ostial take-off angle, and K is a constant.

3. The system of claim 1, wherein the at least one processor is configured to calculate the LSI through the following equation:

$$LSI = \kappa \frac{T \cdot L}{a \cdot \alpha \cdot s \cdot \Delta P}$$

where T is a measure of vessel tortuosity, L is a vessel length, a is a largest second derivative of the three-dimensional (3-D) motion experienced by the vessel, α is an ostial take-off angle, K is a constant, s is a maximum lead body mechanical stress, and ΔP is a blood pressure differential from a tip to an ostium of the vessel.

4. The system of claim 1, wherein the at least one processor is configured to calculate the LSI of the one or more candidate vessels based on motion and anatomical measurements in each of the one more candidate vessels.

5. The system of claim 1, wherein the at least one processor is configured to calculate the LSI of the one or more candidate vessels, at least in part, by accounting for acceleration experienced by the one or more candidate vessels.

6. The system of claim 1, wherein the at least one processor is configured to calculate the LSI of the one or more candidate vessels, at least in part, by accounting for vessel tortuosity.

7. The system of claim 1, wherein the at least one processor is configured to calculate the LSI of the one or more candidate vessels, at least in part, by accounting for vessel length.

8. The system of claim 1, wherein the at least one processor is configured to calculate the LSI of the one or more candidate vessels, at least in part, by accounting for ostial angle.

9. The system of claim 1, wherein the at least one processor is configured to calculate the LSI of the one or more candidate vessels, at least in part, by accounting for (a) acceleration experienced by the one or more candidate vessels, (b) vessel tortuosity, (c) vessel length, and (d) ostial angle.

10. A method for determining a lead placement site within patient anatomy, the method comprising:
calculating a lead stability index (LSI) relating to a lead placement site for one or more candidate vessels; and
displaying data related to the lead placement site, wherein the displaying operation comprises displaying color-coded data related to the one or more candidate vessels.

11. The method of claim 10, wherein the calculating operation comprises calculating the LSI through the following equation:

$$LSI = \kappa \frac{T \cdot L}{a \cdot \alpha}$$

where T is a measure of vessel tortuosity, L is a vessel length, a is a largest second derivative of the three-dimensional (3-D) motion experienced by the vessel, α is an ostial take-off angle, and K is a constant.

12. The method of claim 10, wherein the calculating operation comprises calculating the LSI through the following equation:

$$LSI = \kappa \frac{T \cdot L}{a \cdot \alpha \cdot s \cdot \Delta P}$$

where T is a measure of vessel tortuosity, L is a vessel length, a is a largest second derivative of the three-dimensional (3-D) motion experienced by the vessel, α is an ostial take-off angle, K is a constant, s is a maximum lead body mechanical stress, and ΔP is a blood pressure differential from a tip to an ostium of the vessel.

13. The method of claim 10, wherein the calculating operation comprises accounting for acceleration experienced by the one or more candidate vessels.

14. The method of claim 10, wherein the calculating operation comprises accounting for (a) acceleration experienced by the one or more candidate vessels, (b) vessel tortuosity, (c) vessel length, and (d) ostial angle.

15. A system for determining a lead placement site within patient anatomy, the system comprising:
at least one processor configured to calculate a lead stability index (LSI) relating to a lead placement site for one or more candidate vessels, wherein the at least one processor is configured to calculate the LSI of the one or more candidate vessels, at least in part, by accounting for acceleration experienced by the one or more candidate vessels; and
a display operatively coupled to the at least one processor, wherein the display is configured to show data related to the lead placement site.

16. The system of claim 15, wherein the at least one processor is configured to calculate the LSI through the following equation:

$$LSI = \kappa \frac{T \cdot L}{a \cdot \alpha}$$

where T is a measure of vessel tortuosity, L is a vessel length, a is a largest second derivative of the three-dimensional (3-D) motion experienced by the vessel, $\alpha$ is an ostial take-off angle, and K is a constant.

17. The system of claim 15, wherein the at least one processor is configured to calculate the LSI through the following equation:

$$LSI = \kappa \frac{T \cdot L}{a \cdot \alpha \cdot s \cdot \Delta P}$$

where T is a measure of vessel tortuosity, L is a vessel length, a is a largest second derivative of the three-dimensional (3-D) motion experienced by the vessel, $\alpha$ is an ostial take-off angle, K is a constant, s is a maximum lead body mechanical stress, and $\Delta P$ is a blood pressure differential from a tip to an ostium of the vessel.

18. A method for determining a lead placement site within patient anatomy, the method comprising:
    calculating a lead stability index (LSI) relating to a lead placement site for one or more candidate vessels, wherein the calculating operation comprises accounting for acceleration experienced by the one or more candidate vessels; and
    displaying data related to the lead placement site.

19. The method of claim 18, wherein the calculating operation comprises calculating the LSI through the following equation:

$$LSI = \kappa \frac{T \cdot L}{a \cdot \alpha}$$

where T is a measure of vessel tortuosity, L is a vessel length, a is a largest second derivative of the three-dimensional (3-D) motion experienced by the vessel, $\alpha$ is an ostial take-off angle, and K is a constant.

20. The method of claim 18, wherein the calculating operation comprises calculating the LSI through the following equation:

$$LSI = \kappa \frac{T \cdot L}{a \cdot \alpha \cdot s \cdot \Delta P}$$

where T is a measure of vessel tortuosity, L is a vessel length, a is a largest second derivative of the three-dimensional (3-D) motion experienced by the vessel, $\alpha$ is an ostial take-off angle, K is a constant, s is a maximum lead body mechanical stress, and $\Delta P$ is a blood pressure differential from a tip to an ostium of the vessel.

* * * * *